United States Patent
Cunico et al.

(10) Patent No.: US 10,602,976 B2
(45) Date of Patent: Mar. 31, 2020

(54) PERSONALIZED POSTURE CORRECTION

(71) Applicant: International Business Machines Corporation, Armonk, NY (US)

(72) Inventors: Hernan A. Cunico, Holly Springs, NC (US); Jonathan Dunne, Co. Waterford (IE); Jeremiah O'Connor, Co. Roscommon (IE); Asima Silva, Holden, MA (US)

(73) Assignee: International Business Machines Corporation, Armonk, NY (US)

( * ) Notice: Subject to any disclaimer, the term of this patent is extended or adjusted under 35 U.S.C. 154(b) by 317 days.

(21) Appl. No.: 15/668,090

(22) Filed: Aug. 3, 2017

(65) Prior Publication Data
US 2019/0038215 A1 Feb. 7, 2019

(51) Int. Cl.
*A61B 5/00* (2006.01)
*A61B 5/107* (2006.01)
(Continued)

(52) U.S. Cl.
CPC .......... *A61B 5/4561* (2013.01); *A61B 5/1079* (2013.01); *A61B 5/486* (2013.01);
(Continued)

(58) Field of Classification Search
CPC ..... A61B 5/4561; A61B 5/1079; A61B 5/486; A61B 5/7278; A61B 5/7405; A61B 5/742;
(Continued)

(56) References Cited

U.S. PATENT DOCUMENTS

| 9,141,761 B2 | 9/2015 | Lee |
| 2006/0195051 A1 | 8/2006 | Schnapp et al. |

(Continued)

FOREIGN PATENT DOCUMENTS

| CN | 201928342 | 8/2011 |
| CN | 105761454 | 7/2016 |

(Continued)

OTHER PUBLICATIONS

Ahn et al., Stoop to Conquer: Posture and Affect Interact to Influence Computer Users' Persistence, Springer, Berlin, Heidelberg, https://rd.springer.com/chapter/10.1007/978-3-540-74889-2_51, ACII 2007, LNCS 4738, 2007, 12 pages.

(Continued)

*Primary Examiner* — Robert P Bullington
(74) *Attorney, Agent, or Firm* — Will Stock; Edell, Shapiro & Finnan, LLC (57) ABSTRACT

A method, a system and a computer program product are provided. A posture of an individual is measured while the individual is using an application. The measuring a posture includes making multiple measurements. An amount of time that the individual is using the application is measured. The multiple measurements and the measured amount of time are analyzed to derive a posture quotient. At least one action is performed by a computing device based on the derived posture quotient. The at least one action includes adjusting execution of the application to enable correction of the posture.

20 Claims, 6 Drawing Sheets

(51) Int. Cl.
*G09B 19/00* (2006.01)
*G16H 40/63* (2018.01)
*G16H 20/30* (2018.01)
*G16H 50/30* (2018.01)
*A61B 5/11* (2006.01)
*G09B 5/02* (2006.01)
*G09B 5/04* (2006.01)

(52) U.S. Cl.
CPC ............ *A61B 5/7278* (2013.01); *A61B 5/742* (2013.01); *A61B 5/7405* (2013.01); *A61B 5/746* (2013.01); *G09B 19/00* (2013.01); *G16H 20/30* (2018.01); *G16H 40/63* (2018.01); *G16H 50/30* (2018.01); *A61B 5/1116* (2013.01); *A61B 5/1128* (2013.01); *A61B 2562/0219* (2013.01); *G09B 5/02* (2013.01); *G09B 5/04* (2013.01)

(58) Field of Classification Search
CPC ..... A61B 5/746; A61B 5/1116; A61B 5/1128; A61B 2562/0219; G16H 40/63
USPC ....................................................... 434/247
See application file for complete search history.

(56) References Cited

U.S. PATENT DOCUMENTS

| | | | |
|---|---|---|---|
| 2013/0012790 A1* | 1/2013 | Horseman | G06F 19/3418 600/301 |
| 2013/0072820 A1* | 3/2013 | Lee | A61B 5/1071 600/594 |
| 2016/0174877 A1 | 6/2016 | Meltz et al. | |
| 2016/0262688 A1 | 9/2016 | Nichols et al. | |

FOREIGN PATENT DOCUMENTS

| | | |
|---|---|---|
| WO | 2015007132 | 1/2015 |
| WO | 2016079585 | 5/2016 |

OTHER PUBLICATIONS

Yang et al., Vehicle Driver's ECG and Sitting Posture Monitoring System, https://www.researchgate.net/publication/251910837_Vehicle_Driver%27s_ECG_and_sitting_posture_monitoring_system, Nov. 2009, 4 pages.
Lee et al., Smart Pose: Mobile Posture-aware System for Lowering Physical Health Risk of Smartphone Users, CHI 2013 Extended Abstracts, Apr. 2013, pp. 2257-2266.
Tanaka et al, Nekoze!-Monitoring and detecting head posture while working with laptop and mobile phone, 2015 9th International Conference on Pervasive Computing Technologies for Healthcare (PervasiveHealth), 2015, pp. 237-240.
Goel et al., GripSense: using built-in sensors to detect hand posture and pressure on commodity mobile phones, Proceedings of the 25th annual AC, UIST '12, Oct. 7-10, 2012, Cambridge, Massachusetts, USA, pp. 545-554.
Anonymous, Is Your Smartphone Giving you Bad Posture?, FirstStateSpine, A Division of First State Orthopaedics, Jun. 1, 2015, 2 pages.
Firger, OMG, You're Texting Your Way to Back Pain, CBS News, Nov. 14, 2014, 7 pages.
Ward, Children 'Becoming Hunchbacks' Due to Addictions to Smart Phones, The Telegraph, Oct. 16, 2015, 16 pages.
Sloane, 'Text Neck' and Other Tech Troubles, Pain Management Health Center, WebMD Health News, Nov. 26, 2014, 4 pages.
Havemen et al., Smart Monitoring of Worker Posture in an Office Environment, Nov. 2017, pp. 1-17.
Derogatis, Stop the Slouch: 5 Apps to Improve Your Posture, http://www.refinery29.com/posture-apps, Mar. 1, 2014, 37 pages.
Anonymous, Climb the Strategy Ladder to Script Your Victory in Brawl Stars Game, Altchi Gaming Borders, Sep. 17, 2017, 15 pages.

* cited by examiner

| USER | AGE | INIT POS | DISTANCE FROM MONITOR (CM) | HEAD/MONITORING ANGLE (DEGREES) | DESK HEIGHT (CM) | CHAIR HEIGHT | APP USAGE | POSTURE QUOTIENT |
|---|---|---|---|---|---|---|---|---|
| JOHN | 25 | SITTING | 35 | 20 | 72 | 55 | 60 MINS | 0.456 |
| MARY | 15 | STANDING | 12 | 14 | N/A | N/A | 120 MINS | 0.889 |
| JAMES | 21 | SITTING | 21 | 25 | 65 | 41 | 45 MINS | 0.683 |

PERSONALIZED POSTURE CORRECTION

BACKGROUND

Field of the Invention

Present invention embodiments are related to systems, methods and computer program products for determining whether a user of a computing device is exhibiting poor posture and performing an action when poor posture is detected.

Description of Related Art

Back and neck pain are a pervasive problem. The media has provided numerous reports about muscle problems caused by poor posture. The reports are not only about muscle problems in adults caused by poor posture, but an increasing number of the reports are about children with muscle problems caused by poor posture.

It is challenging for one to self-diagnose poor posture because one may not be aware of the poor posture until moving out of a given position or experiencing back or neck pain.

SUMMARY

In a first aspect of the invention, a machine-implemented method is provided for minimizing effects of incorrect postures for an individual. A sensing device measures a posture of the individual while the user uses an application. The measuring of the posture includes making multiple measurements. The sensing device measures an amount of time that the individual uses the application. A computing device analyzes the multiple measurements and the measured amount of time the individual uses the application to derive a posture quotient. The computing device performs at least one action based on the derived posture quotient, wherein the at least one action includes adjusting execution of the application to enable correction of the posture.

In a second aspect of the invention, a system for minimizing effects of incorrect postures for an individual is provided. The system includes a computing device having at least one processor, at least one memory connected with the at least one processor, and a camera connected with the at least one processor. The at least one processor is configured to: measure a posture of the individual while the individual uses an application, wherein the measuring a posture includes making multiple measurements; measure an amount of time the individual uses the application; analyzing the multiple measurements and the measured amount of time the individual uses the application to derive a posture quotient; and performing at least one action based on the derived posture quotient, wherein the at least one action includes adjusting execution of the application to enable correction of the posture.

In a third aspect of the invention, a computer program product is provided. The computer program product includes at least one computer readable storage medium having computer readable program code embodied therewith for execution on at least one processor. The computer readable program code is configured to be executed by the at least one processor to: measure a posture of an individual while the individual uses an application, wherein the measuring a posture includes making multiple measurements; measure an amount of time the individual uses an application; analyze the multiple measurements and the measured amount of time that the individual uses the application to derive the posture quotient; and performing at least one action based on the derived posture quotient, wherein the at least one action includes adjusting execution of the application to enable correction of the posture.

BRIEF DESCRIPTION OF THE DRAWINGS

Generally, like reference numerals in the various figures are utilized to designate like components.

DETAILED DESCRIPTION

Present invention embodiments include methods, systems and computer program products for determining whether an individual using an application on a computing device is exhibiting bad posture. If the individual is exhibiting bad posture, the computing device may perform an action based on a severity of the exhibited bad posture and an amount of time the individual is using the application. In some embodiments, the computing device may access the individual's health information, with the individual's permission, and may consider the individual's health information, in addition to the exhibited bad posture and the amount of time the individual is using the application, when determining the action to perform.

The possible actions that the computing device may perform may include one or more alerting actions and/or one or more remedial actions. The alerting actions may include, but not be limited to: alerting the individual by a visual or an audio cue; providing an alert to the individual regarding one or more recommendations for improving posture; providing personalized alerts to the individual based, at least partially, on health information of the individual; and providing an alert to another individual based on the other individual having similar health information. The remedial actions may include, but not be limited to: dimming a display of the computing device; performing posture realignment checks every predetermined time interval and adjusting execution of the application (e.g., suspending use of the application for a predetermined amount of time, suspending the use of the application until the individual corrects the posture, slowing execution of the application, etc.).

Figure 1:
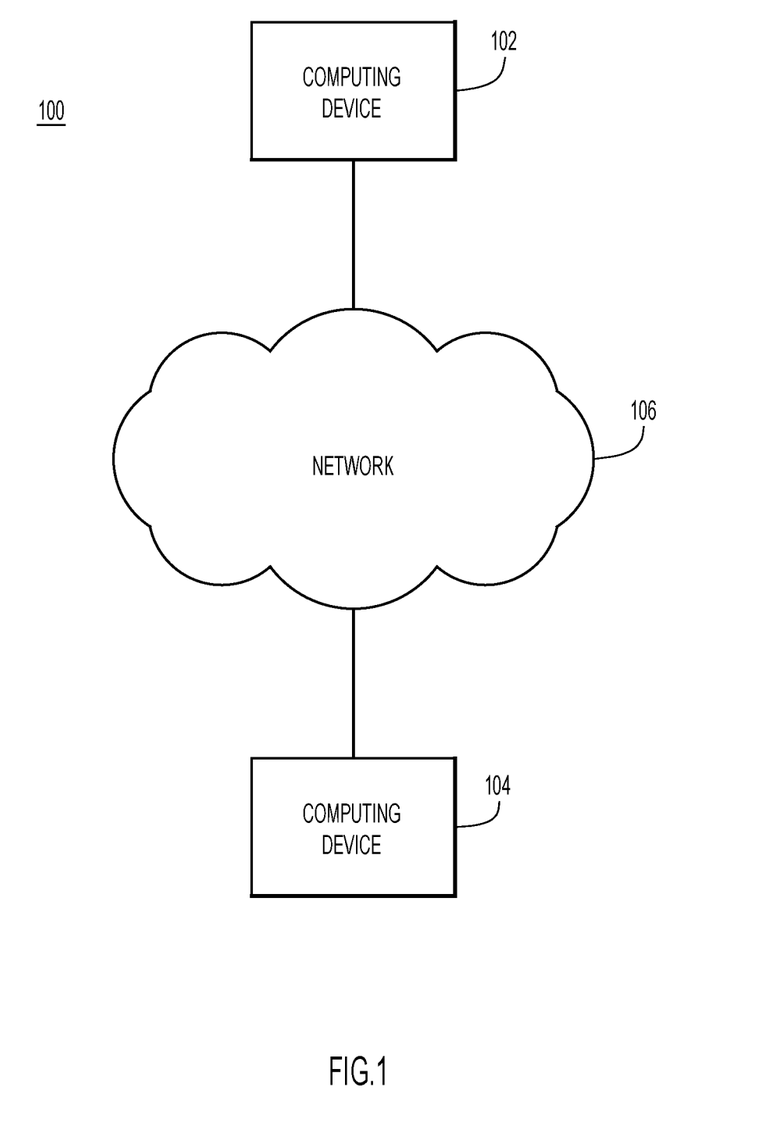
FIG. 1 illustrates an example environment in which various embodiments may operate.

FIG. 1 shows an example environment 100 in which various embodiments may operate. Environment 100 may include computing device 102, computing device 104 and network 106. Computing device 102 may include, but not be limited to, a smart phone, a tablet computing device, a laptop computing device, a desktop computing device, or other type computing device. Computing device 104 may include, but not limited to, a desktop computing device, a mainframe computing device, a laptop computing device, a plurality of computing devices configured as a server farm, or other type of computing device. Network 106 may include, but not limited to, a wireless network, a wired network, a local area network, a wide area network, a plurality of networks, the Internet, or a combination of networks. Other embodiments may operate in a standalone environment.

Figure 2:
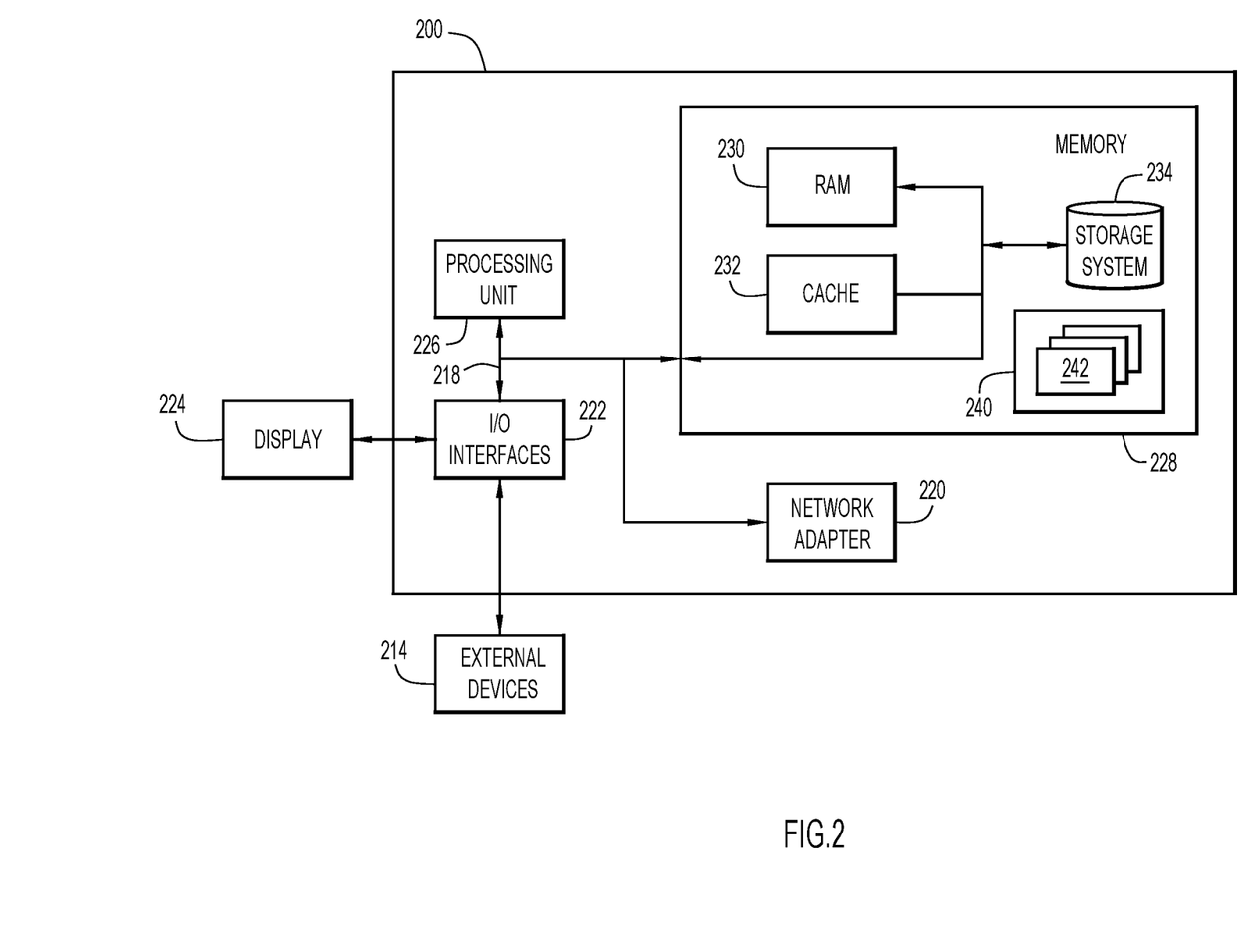
FIG. 2 is a functional block diagram of a computing system that may implement one or more computing devices according to various embodiments.

FIG. 2 is a functional block diagram of a computing system 200 that may implement computing device 102 or computing device 104 in various embodiments of the invention. Computing system 200 is shown in a form of a general-purpose computing device. Components of computing system 200 may include, but are not limited to, one or more processors or processing units 216, a system memory 228, and a bus 218 that couples various system components including system memory 228 to one or more processors 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computing system 200 typically includes a variety of computer system readable media. Such media may be any available media that is accessible by computing system 200, and may include both volatile and non-volatile media, removable and non-removable media.

System memory 228 can include computer system readable media in the form of volatile memory, such as random access memory (RAM) 230 and/or cache memory 232. Computing system 200 may further include other removable/non-removable, volatile/non-volatile computer system storage media. By way of example only, storage system 234 can be provided for reading from and writing to a non-removable, non-volatile magnetic media (not shown and typically called a "hard drive"). In some embodiments, storage system 234 may include a database system. Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computing system 200 may also communicate with one or more external devices 214 such as a keyboard, a pointing device, a display 224, etc.; one or more devices that enable a user to interact with computing system 200; and/or any devices (e.g., network card, modem, etc.) that enable computing system 200 to communicate with one or more other computing devices. Such communication can occur via Input/Output (I/O) interfaces 222. Still yet, computing system 200 may communicate with one or more networks such as a local area network (LAN), a general wide area network (WAN), and/or a public network (e.g., the Internet) via network adapter 220. As depicted, network adapter 220 communicates with the other components of computing system 200 via bus 218. It should be understood that, although not shown, other hardware and/or software components could be used in conjunction with computing system 200. Examples, include, but are not limited to: a camera, an accelerometer, a gyroscope, microcode, device drivers, redundant processing units, external disk drive arrays, RAID systems, tape drives, and data archival storage systems, etc.

Figure 3:
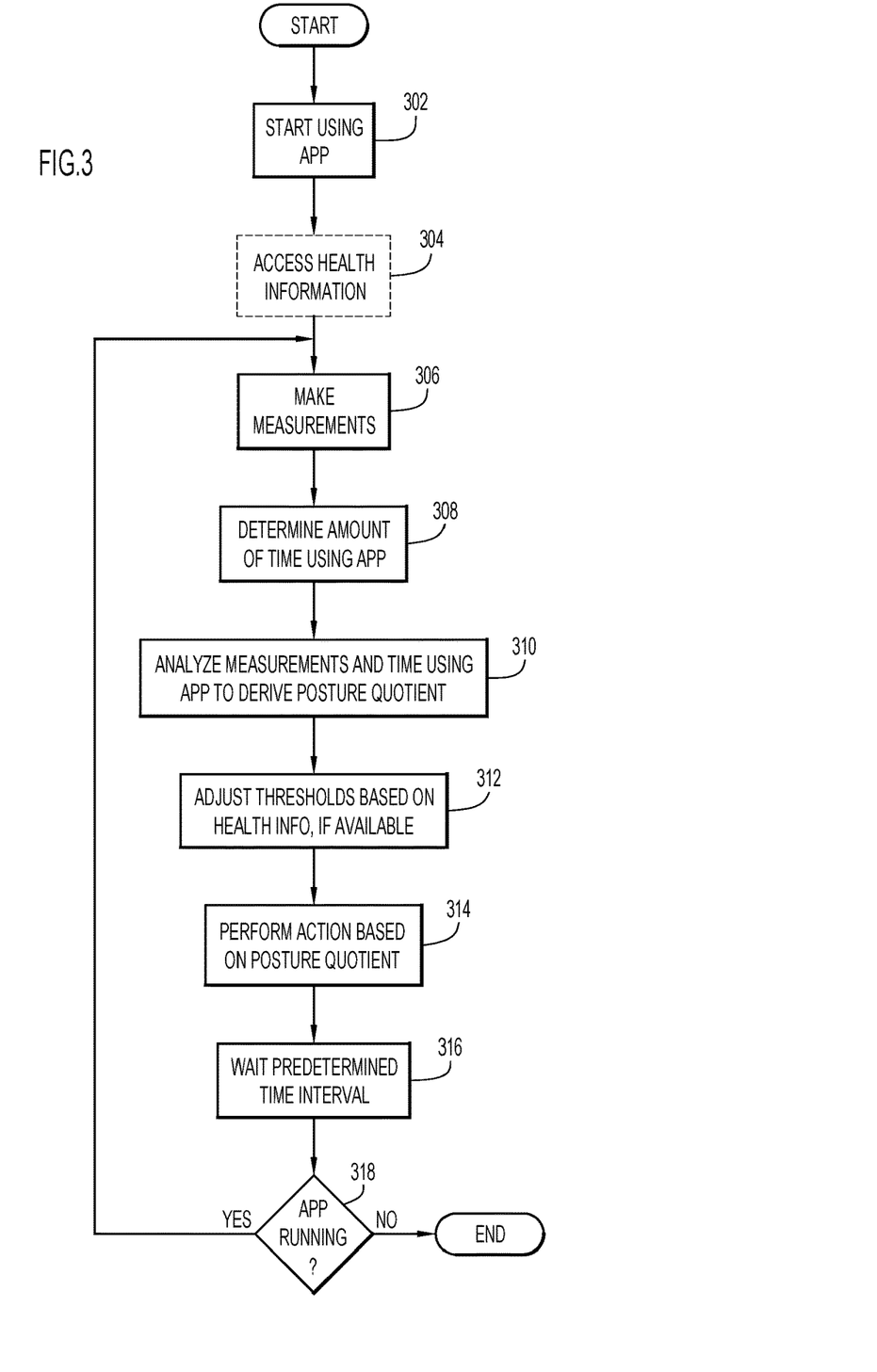
FIG. 3 is a flowchart that explains a process that may be performed according to a number of embodiments.

FIG. 3 is a flowchart of an example process that may be performed by computing device 102 in a number of embodiments. The process may begin with an individual starting to use an application on computing device 102 (act 302). Optionally, in some embodiments, computing device 102 may access health information of the individual over network 106 from various data sources, assuming that the individual previously authorized access to the health information (act 304). Next, computing device 102, may make a number of measurements to determine a posture of the individual (act 306). The computing device may include various sensing devices to perform the measurements (e.g., camera/image analysis, accelerometers, gyroscopes or other sensors, etc.)

Figure 4:
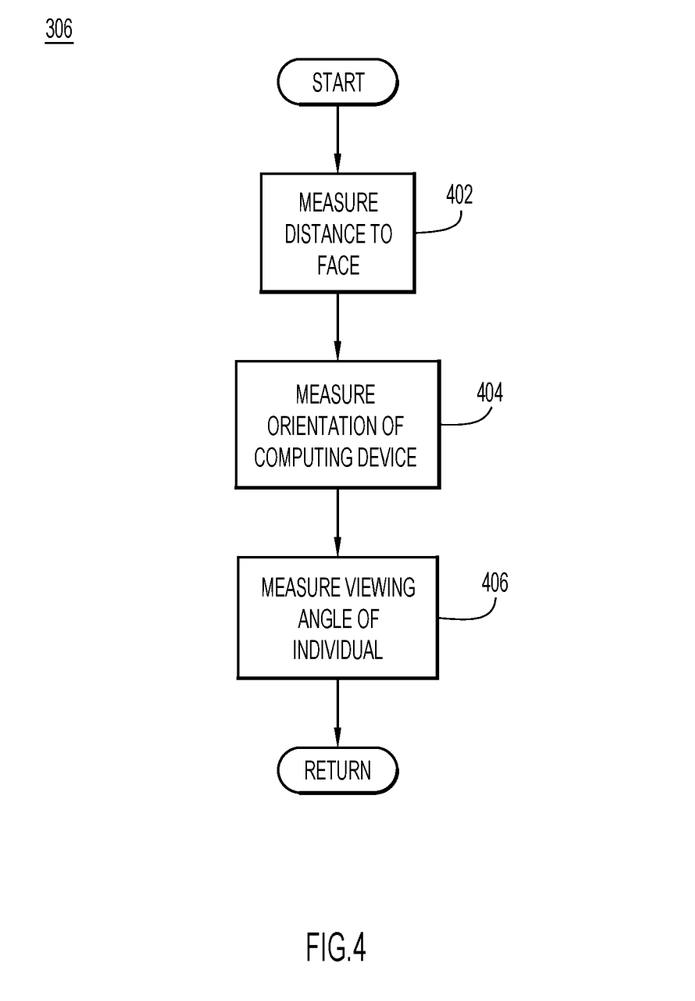
FIG. 4 is a flowchart that illustrates an example process for making multiple measurements according to various embodiments.

FIG. 4 is a flowchart of an example process for making the measurements of act 306. The process may begin with computing device 102 measuring a distance from a display of computing device 102 to a face of the individual (act 402). In some embodiments, this may be accomplished by using a front-facing camera included in the device, capturing an image of the face of the individual and determining the distance from the display of computing device 102 to the face based on pixel density of the face in the image. Other methods for measuring the distance from the display to face may be used in other embodiments.

Next, computing device 102 may measure its orientation based on readings from sensors included in computing device 102 such as, for example, an accelerometer and a gyroscope (act 404). Computing device 102 may determine a viewing angle of the individual based on the orientation of computing device 102 and a position of eyes of the individual captured by the camera of computing device 102 (act 406).

Returning to FIG. 3, computing device 102 may determine an amount of time the individual is using the application (act 308) and may analyze the measurements and the amount of time to determine a posture quotient for the individual (act 310). Optionally, during act 310, if the health information (e.g., spinal health issues, vision problems, muscle problems, etc.) is provided, computing device 102 may analyze the health information. In some embodiments, computing device 102 may send the measurements and the amount of time to computing device 104 via network 106 for computing device 104 to determine the posture quotient and return the posture quotient to computing device 102. In other embodiments, computing device 102 may analyze the measurements and determine the posture quotient. In some embodiments, the health information may be stored in a central database such as, for example, a database accessed by computing device 104. In such embodiments, computing device 104 may analyze the health information and provide a result of the analysis to computing device 102 through network 106. Alternatively, computing device 104 may analyze measurements received from computing device 102 and health information of the individual accessible by computing device 104 to determine the posture quotient, which may be returned to computing device 102.

Figure 5:
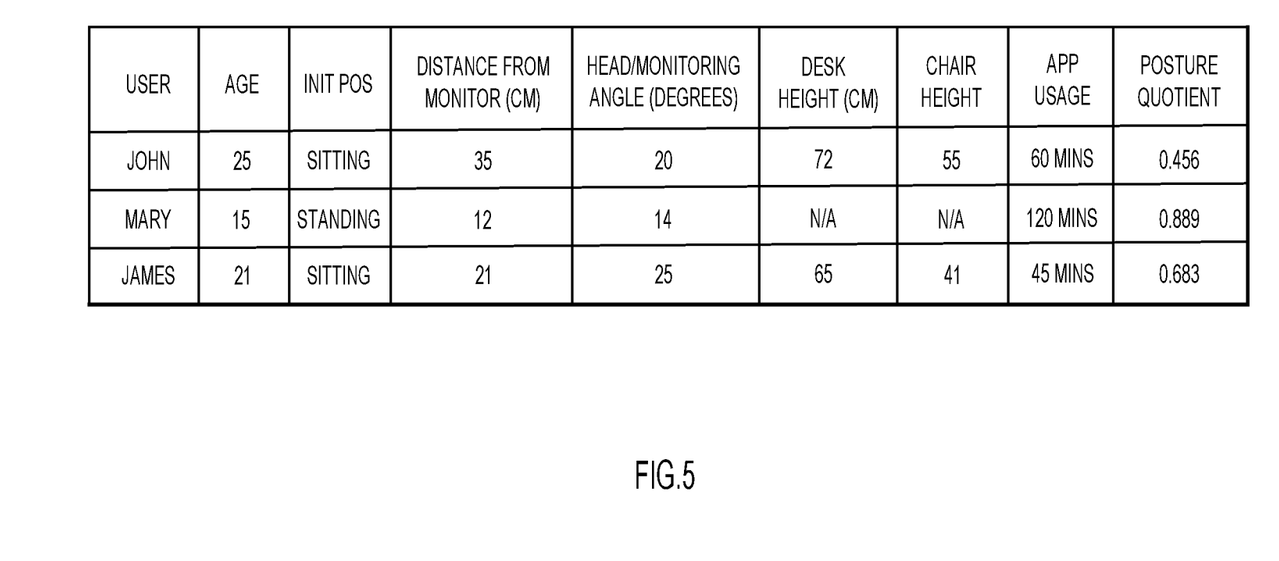
FIG. 5 shows an example table of measurements along with derived posture quotients for multiple users.

FIG. 5 shows a table of example measurements demonstrating how a posture quotient may be derived. Through regression analysis, a sample model may be calculated. By way of example, a model may include: y=0.008161696+(0.4456×user)+(−0.111×age)+(0.44×init_pos)+(0.678×dist_mon)+(0.987×head_angle)+(−0.151311111×desk_height)(0.235×chair_height)+(−0.799×app_usage), where 0.008161696, 0.4456, −0.111, 0.44, 0.678, 0.987, 0.235 and −0.799 are values derived through the regression analysis. Using the values pertaining to James in FIG. 5 and assuming a weight of 0.5 for user James to indicate a person with medium injury proneness and a weight of 0.25 for initial position to indicate sitting, we have:

$$y = \ln\left(\frac{p}{1-p}\right) = 0.008161696 + (0.4456 \times 0.5) +$$
$$(-0.111 \times 21) + (0.44 \times 0.25) + (0.678 \times 21) + (0.987 \times 25) +$$
$$(-0.151311111 \times 65) + (0.235 \times 41) + (-0.799 \times 45)$$
$$\ln\left(\frac{p}{1-p}\right) = 0.008161696 + 0.2228 - 2.331 + 0.11 + 14.238 +$$
$$24.675 - 9.835222215 + 9.635 - 35.955 = 0.767739481$$
$$\frac{p}{1-p} = e^{0.767739481} = 2.15488958$$
$$p = \frac{2.15488958}{3.15488958} = 0.6830$$

Therefore, the posture quotient, p, is 0.6830 for this example. In some embodiments the regression analysis may be a binary regression analysis.

Based on a result of analyzing the health information, thresholds may be adjusted (act 312). The thresholds are used during act 314 to determine which action(s) to perform, if any, based on the posture quotient. In some embodiments, default thresholds may be set to: 0.456 for moderate posture strain; 0.679 for strong posture strain; and 0.889 for severe posture strain. For example, if the health information is provided and indicates back or neck problems or related muscle issues, then the thresholds may be adjusted during act 312 (e.g., based on predefined values or adjustments, etc.) to, for example: 0.302 for moderate posture strain; 0.510 for strong posture strain; and 0.745 for severe posture strain. In other embodiments, different threshold values and/or a different number of thresholds may be used.

Figure 6:
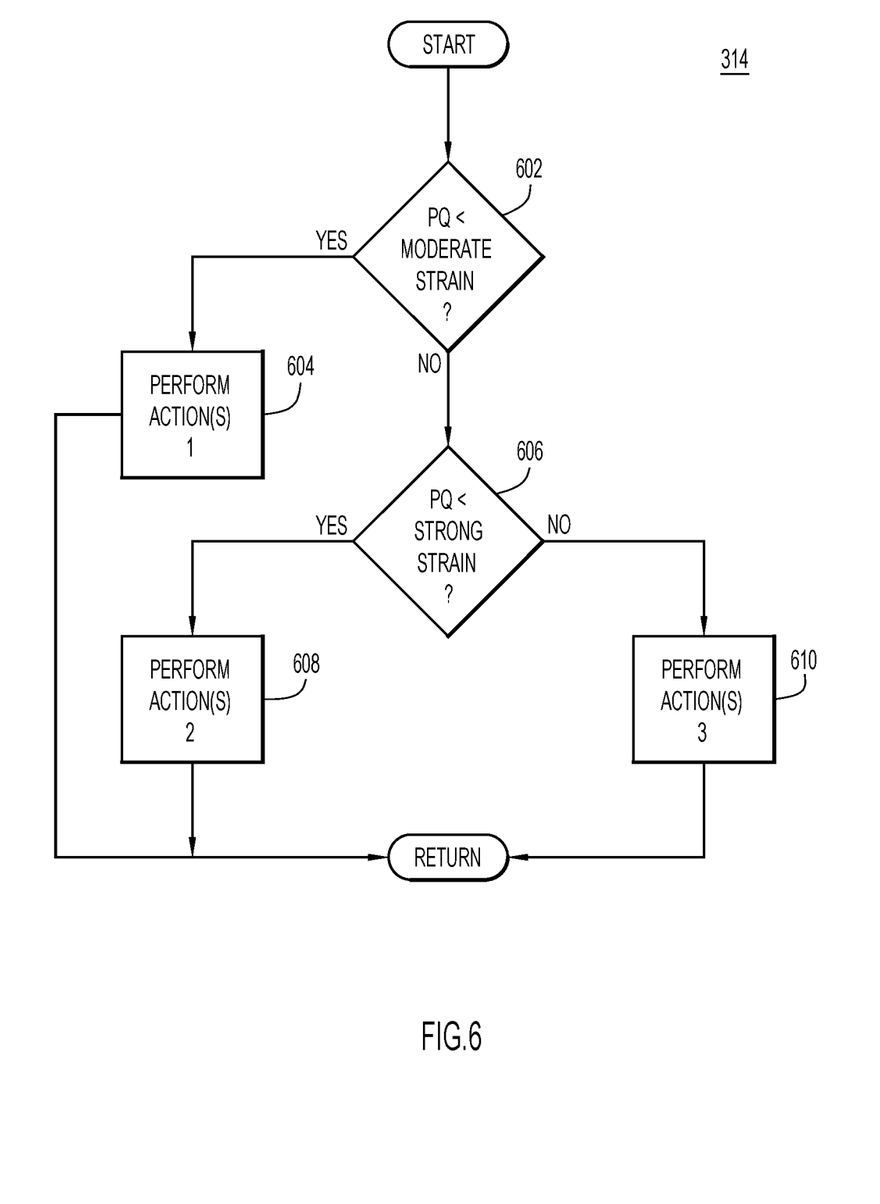
FIG. 6 is a flowchart that explains an example process of determining one or more actions to perform based on a derived posture quotient and performing the determined one or more actions according to various embodiments.

FIG. 6 is a flowchart of a process for performing act 314 in computing device 102 in more detail. The process may begin with computing device 102 determining whether the posture quotient is less than the moderate strain threshold (act 602). If the posture quotient is determined to be less than the moderate strain threshold, then computing device 102 may perform one or more actions as indicated by act 604. The actions of act 604 may include one or more alert actions, which may include visual and audio cues. An example of alert actions may include, but not be limited to: providing a visual and/or audio alert to the individual including recommendations for improving posture; providing one or more personalized visual and/or audio alerts based, at least partially, on health information of the individual; providing an alert to another individual based on similarities to the individual; and provide a visual and/or audio alert to the individual every predetermined time period suggesting a movement break. The predetermined time period may be 15 minutes or another suitable time period in other embodiments.

The following are examples of the above-mentioned alerts. In other embodiments, other visual and/or audio cues may be provided to the individual. A visual cue may include text displayed on a display screen of computing device 102, a text message sent to the individual or an email sent to the individual. An audio cue may include the playing of one or more particular sounds and/or a computer-generated voice playing audio including words such as, for example, "You are showing signs of moderate strain. I will remind you to take a movement break every 15 minutes." Another audio and/or visual alert may indicate to the individual, "You are exhibiting signs of severe posture strain. I will check your posture every 15 minutes."

If, during act 602, the posture quotient is determined to be greater than or equal to the moderate strain threshold, then a determination may be made regarding whether the posture quotient is less than the strong strain threshold (act 606). If the posture quotient is determined to be less than the strong strain threshold, then one or more alerts and/or remedial actions may be performed (act 608). In some embodiments, the alert actions of act 608 may include, but not be limited to, providing a visual or audio alert reminding the individual to take a movement break every predetermined time interval such as, for example, every 15 minutes or another time interval. In these embodiments, the remedial actions may include, but not be limited to, pausing execution of the application for a predetermined time interval such as, for example 5 minutes or another suitable time interval. In other embodiments, other alert actions and/or remedial actions may be performed.

If, during act 606, the posture quotient is determined to be greater than or equal to the strong strain threshold, then one or more alert and/or remedial actions may be performed by computing device 102 (act 610). For example, the alert actions may include, but not be limited to, providing a visual or audio alert informing the user to realign his or her posture. The remedial actions may include, but not be limited to, dimming the display of computing device 102 for a set period of time and permitting the user to resume using the application only after a realignment check confirms that the posture of the individual is realigned. In other embodiments, other actions may be performed when the posture quotient is determined to be not less than the severe strain threshold.

In a variation of the above-mentioned embodiments, other individuals, who authorized use of their health information which indicates similar health issues to those of the individual using the application, may be provided with a visual or auditory alert similar to those of the individual using the application. For example, another individual who has a lumbar issue similar to the individual using the application and who is associated with that individual through a social media application, may receive a visual or audio alert such as, for example, an alert informing the another individual that he or she should take a movement break every predetermined time interval.

The above-mentioned embodiments may adjust thresholds based on analysis of provided health information. In other embodiments, provided health information may be used for machine learning to train computing device 102 or computing device 104. As a result of the training, a derived model may produce a posture quotient for an individual that need not be adjusted later, based on the health information.

In addition to alerts being provided to individuals, other embodiments may provide visual or audio information that may be useful to the individuals using the application. For example, users showing signs of strain due to bad posture may be provided with information regarding medical providers, including, but not limited to, chiropractors, orthopedic specialists, etc. Information regarding relevant medical treatments may also be provided, such as, physical therapy, spinal surgery, or other treatments.

The environment of present invention embodiments may include any number of computers or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and may communicate via any suitable communications medium (e.g., LAN, WAN, Intranet, Internet, hardwired, modem connection, wireless, etc.). For example, the functions of the present invention embodiments may be distributed in any manner among the various systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to a server and/or client systems. The database systems and/or storage structures may be remote from or local to the computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media)

having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

We claim:

1. A method for minimizing effects of incorrect postures for an individual, the method comprising:
    measuring, by a sensing device, a posture of the individual while using an application, the measuring a posture including making a plurality of measurements, the measuring further comprising:

capturing an image of a face of the individual with a camera included in a computing device having a display, determining, by the computing device, a distance of the face from the display of the computing device based on a pixel density of the face in the image, measuring, based on readings from an accelerometer and a gyroscope included in the computing device, an orientation of the computing device, and determining, by the computing device, a viewing angle of the individual based on the orientation of the computing device and a position of eyes of the individual captured by the camera;

measuring, by the sensing device, an amount of time the individual is using the application;

analyzing, by one of the computing device and a second computing device, the plurality of measurements and the measured amount of time the individual is using the application to derive a posture quotient, the plurality of measurements including the distance of the face from the display, the orientation of the computing device, and the viewing angle of the individual; and performing, by the computing device, at least one action based on the derived posture quotient, the at least one action including adjusting execution of the application to enable correction of the posture.

2. The method of claim 1, wherein the analyzing further comprises:

accessing health information of the individual with a permission of the individual; and analyzing the accessed health information to determine the posture quotient.

3. The method of claim 1, wherein the deriving the posture quotient comprises:

using the plurality of measurements and the measured amount of time the individual is using the application with parameters derived by performing a regression analysis with respect to measurement data regarding usage of the application by a plurality of individuals; and applying the plurality of measurements and the measured amount of time the individual is using the application to the derived parameters to determine the posture quotient.

4. The method of claim 1, wherein the at least one action comprises a plurality of alerting actions including one or more from a group of:

alerting the individual by visual or audio cues, providing an alert to the individual regarding recommendations, providing personalized alerts to the individual based, at least partially, on health information of the individual, and providing an alert to another individual based on similarities to the individual.

5. The method of claim 1, wherein the at least one action comprises remedial actions including one or more from a group of:

dimming the display, performing posture realignment checks every predetermined time interval, suspending use of the application for a predetermined amount of time, and suspending the use of the application until the individual corrects the posture.

6. The method of claim 1, further comprising:

performing more invasive remedial actions as the posture quotient indicates increasing severity of posture issues.

7. A system for minimizing effects of incorrect posture for an individual, the system comprising:

a computing device comprising:

at least one processor, at least one memory connected with the at least one processor, an accelerometer connected with the at least one processor, a gyroscope connected with the at least one processor, and a camera connected with the at least one processor, wherein the at least one processor is configured to perform:

measuring a posture of the individual while using an application, the measuring a posture including making a plurality of measurements, the measuring further comprising:

capturing an image of a face of the individual with the camera of the computing device having a display, determining a distance of the face from the display of the computing device based on a pixel density of the face in the image, measuring, based on readings from the accelerometer and the gyroscope included in the computing device, an orientation of the computing device, and determining a viewing angle of the individual based on the orientation of the computing device and a position of eyes of the individual captured by the camera;

measuring an amount of time the individual is using the application;

analyzing the plurality of measurements and the measured amount of time the individual is using the application to derive a posture quotient, the plurality of measurements including the distance of the face from the display, the orientation of the computing device, and the viewing angle of the individual; and performing at least one action based on the derived posture quotient, the at least one action including adjusting execution of the application to enable correction of the posture.

8. The system of claim 7, wherein the analyzing further comprises:

accessing health information of the individual with a permission of the individual; and analyzing the accessed health information to determine the posture quotient.

9. The system of claim 7, wherein the deriving the posture quotient comprises:

using the plurality of measurements and the measured amount of time the individual is using the application with parameters derived by performing a regression analysis with respect to measurement data regarding usage of the application by a plurality of individuals; and applying the plurality of measurements and the measured amount of time the individual is using the application to the derived parameters to determine the posture quotient.

10. The system of claim 7, wherein the at least one action comprises a plurality of actions including one or more from a group of:

alerting the individual by visual or audio cues,
providing an alert to the individual regarding recommendations,
providing personalized alerts to the individual based, at least partially, on health information of the individual, and
providing an alert to another individual based on similarities to the individual.

11. The system of claim 7, wherein the at least one action comprises remedial actions including one or more from a group of:
dimming the display,
performing posture realignment checks every predetermined time interval,
suspending use of the application for a predetermined amount of time, and
suspending the use of the application until the individual corrects the posture.

12. The system of claim 7, wherein the at least one processor is further configured to:
perform more invasive remedial actions as the posture quotient indicates increasing severity of posture issues.

13. A computer program product comprising:
at least one computer readable storage medium having computer readable program code embodied therewith for execution on at least one processor, the computer readable program code being configured to be executed by the at least one processor to perform:
measuring a posture of an individual while using an application, the measuring a posture including making a plurality of measurements, the measuring further comprising:
capturing an image of a face of the individual with a camera included in a computing device having a display,
determining, by the computing device, a distance of the face from the display of the computing device based on a pixel density of the face in the image,
measuring, based on readings from an accelerometer and a gyroscope included in the computing device, an orientation of the computing device, and
determining a viewing angle of the individual based on the orientation of the computing device and a position of eyes of the individual captured by the camera;
measuring an amount of time the individual is using the application;
analyzing the plurality of measurements and the measured amount of time the individual is using the application to derive a posture quotient, the plurality of measurements including the distance of the face from the display, the orientation of the computing device, and the viewing angle of the individual; and
performing at least one action based on the derived posture quotient, the at least one action including adjusting execution of the application to enable correction of the posture.

14. The computer program product of claim 13, wherein the analyzing further comprises:
accessing health information of the individual with a permission of the individual; and
analyzing the accessed health information to determine the posture quotient.

15. The computer program product of claim 13, wherein the deriving the posture quotient comprises:
using the plurality of measurements and the measured amount of time the individual is using the application with parameters derived by performing a regression analysis with respect to measurement data regarding usage of the application by a plurality of individuals; and
applying the plurality of measurements and the measured amount of time the individual is using the application to the derived parameters to determine the posture quotient.

16. The computer program product of claim 13, wherein the at least one action comprises a plurality of actions including one or more from a group of:
alerting the individual by visual or audio cues,
providing an alert to the individual regarding recommendations,
providing personalized alerts to the individual based, at least partially, on health information of the individual, and
providing an alert to another individual based on similarities to the individual.

17. The computer program product of claim 13, wherein the at least one action comprises remedial actions including one or more from a group of:
dimming the display,
performing posture realignment checks every predetermined time interval,
suspending use of the application for a predetermined amount of time, and
suspending the use of the application until the individual corrects the posture.

18. The method of claim 2, wherein the analyzing further comprises:
adjusting posture quotient thresholds based on the accessed health information, wherein
the posture quotient thresholds are used to determine the at least one action to perform.

19. The system of claim 8, wherein the analyzing further comprises:
adjusting posture quotient thresholds based on the accessed health information, wherein
the posture quotient thresholds are used to determine the at least one action to perform.

20. The computer program product of claim 14, wherein the analyzing further comprises:
adjusting posture quotient thresholds based on the accessed health information, wherein
the posture quotient thresholds are used to determine the at least one action to perform.

* * * * *